(12) United States Patent
Becker et al.

(10) Patent No.: US 10,791,966 B2
(45) Date of Patent: Oct. 6, 2020

(54) PATIENT HANDLING DEVICE INCLUDING LOCAL STATUS INDICATION, ONE-TOUCH FOWLER ANGLE ADJUSTMENT, AND POWER-ON ALARM CONFIGURATION

(71) Applicant: Stryker Corporation, Kalamazoo, MI (US)

(72) Inventors: David Terrance Becker, Grand Rapids, MI (US); Christopher John Hopper, Kalamazoo, MI (US); Michael Joseph Hayes, Kalamazoo, MI (US); Vivek Shankar, San Diego, VA (US); Richard C. Mayoras, Jr., Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 944 days.

(21) Appl. No.: 14/488,705

(22) Filed: Sep. 17, 2014

(65) Prior Publication Data
US 2015/0000035 A1    Jan. 1, 2015

Related U.S. Application Data

(63) Continuation of application No. 14/165,308, filed on Jan. 27, 2014, now Pat. No. 8,844,076, which is a
(Continued)

(51) Int. Cl.
*A61B 5/11*  (2006.01)
*A61B 5/00*  (2006.01)
(Continued)

(52) U.S. Cl.
CPC ............ *A61B 5/1115* (2013.01); *A61B 5/002* (2013.01); *A61B 5/1117* (2013.01);
(Continued)

(58) Field of Classification Search
CPC ......................... A61G 7/00; A61G 7/002–018
See application file for complete search history.

(56) References Cited

U.S. PATENT DOCUMENTS 3,599,199 A    8/1971  Bunting
3,913,153 A *  10/1975  Adams ................... A61G 7/018
                                                    318/65
(Continued)

FOREIGN PATENT DOCUMENTS

EP    1 199 027 A2    4/2002
EP    1 354 539 A1    10/2003
(Continued)

OTHER PUBLICATIONS

Plexus Medical Service Manual for 02 Zoned C4000 Portable Rotation System and CareMedx C5000 Multi-zoned Low Air Loss Therapy System, Apr. 2003.
(Continued)

*Primary Examiner* — Peter M. Cuomo
*Assistant Examiner* — Ifeolu A Adeboyejo
(74) *Attorney, Agent, or Firm* — Warner Norcross + Judd LLP

(57) ABSTRACT

A patient handling device includes a deck for supporting a patient support surface, a controller, and two light sources, which are operable to output light of different colors. The controller is in communication with the light sources and operable to monitor the plurality of conditions and to generate a first unified indication by illuminating one of the lights when all the conditions remain in their desired state, and to generate a second indication by illuminating the other light when any of the conditions change from their desired state.

20 Claims, 11 Drawing Sheets

Related U.S. Application Data continuation of application No. 11/557,349, filed on Nov. 7, 2006, now Pat. No. 8,689,376.

(60) Provisional application No. 60/734,073, filed on Nov. 7, 2005.

(51) Int. Cl.

| | | |
|---|---|---|
| *A61G 7/05* | (2006.01) | |
| *A61B 90/30* | (2016.01) | |
| *A61G 7/015* | (2006.01) | |
| *A61G 7/018* | (2006.01) | |
| *A61G 7/012* | (2006.01) | |
| *G08B 21/22* | (2006.01) | |

(52) U.S. Cl.
CPC ............ *A61B 5/6887* (2013.01); *A61B 90/30* (2016.02); *A61G 7/012* (2013.01); *A61G 7/015* (2013.01); *A61G 7/018* (2013.01); *A61G 7/0507* (2013.01); *A61G 7/0509* (2016.11); *A61G 7/0514* (2016.11); *A61G 7/0516* (2016.11); *A61G 7/0524* (2016.11); *G08B 21/22* (2013.01); *A61B 5/6891* (2013.01); *A61B 2090/309* (2016.02); *A61G 2203/42* (2013.01); *Y10S 5/905* (2013.01)

(56) References Cited

U.S. PATENT DOCUMENTS

| | | | |
|---|---|---|---|
| 4,044,286 A * | 8/1977 | Adams | A61G 7/018 |
| | | | 318/103 |
| 4,067,005 A | 1/1978 | Levy et al. | |
| 4,094,024 A * | 6/1978 | Benoit | A61G 7/018 |
| | | | 192/48.9 |
| 4,159,496 A * | 6/1979 | Stevens | A61G 7/018 |
| | | | 307/115 |
| 4,196,425 A | 4/1980 | Williams, Jr. et al. | |
| 4,264,904 A | 4/1981 | McCoy et al. | |
| 4,295,133 A | 10/1981 | Vance | |
| 4,633,237 A | 12/1986 | Tucknott et al. | |
| 4,700,180 A | 10/1987 | Vance | |
| 4,882,566 A | 11/1989 | Koerber, Sr. et al. | |
| 4,907,845 A | 3/1990 | Wood | |
| 4,998,939 A | 3/1991 | Potthast et al. | |
| 5,137,033 A | 8/1992 | Norton | |
| 5,195,198 A | 3/1993 | Travis | |
| 5,276,432 A | 1/1994 | Travis | |
| 5,319,355 A | 6/1994 | Russek | |
| 5,319,363 A | 6/1994 | Welch et al. | |
| 5,393,938 A | 2/1995 | Bumbalough | |
| 5,411,457 A | 5/1995 | Hartdegen, III et al. | |
| 5,450,639 A | 9/1995 | Weismiller et al. | |
| 5,664,270 A | 9/1997 | Bell et al. | |
| 5,689,839 A | 11/1997 | Laganiere et al. | |
| 5,699,038 A | 12/1997 | Ulrich et al. | |
| 5,774,914 A | 7/1998 | Johnson et al. | |
| 6,000,076 A * | 12/1999 | Webster | A61G 7/015 |
| | | | 5/600 |
| 6,014,346 A | 1/2000 | Malone | |
| 6,014,784 A | 1/2000 | Taylor et al. | |
| 6,240,579 B1 | 6/2001 | Hanson et al. | |
| 6,320,510 B2 | 11/2001 | Menkedick et al. | |
| 6,822,571 B2 | 11/2004 | Conway | |
| 6,829,796 B2 | 12/2004 | Salvatini et al. | |
| 7,533,429 B2 | 5/2009 | Menkedick et al. | |
| 7,594,286 B2 | 9/2009 | Williams | |
| 8,117,701 B2 | 2/2012 | Bobey et al. | |
| 8,464,380 B2 | 6/2013 | Bobey et al. | |
| 2002/0059679 A1 | 5/2002 | Weismiller et al. | |
| 2004/0103475 A1 | 6/2004 | Ogawa et al. | |
| 2005/0035871 A1 | 2/2005 | Dixon et al. | |
| 2006/0049936 A1 | 3/2006 | Collins, Jr. et al. | |
| 2006/0101581 A1 | 5/2006 | Blanchard et al. | |
| 2006/0279427 A1 | 12/2006 | Becker et al. | |
| 2007/0076852 A1 | 4/2007 | Ishikawa et al. | |
| 2007/0210917 A1 | 9/2007 | Collins, Jr. et al. | |

FOREIGN PATENT DOCUMENTS

| | | |
|---|---|---|
| EP | 1 477 110 A1 | 11/2004 |
| WO | WO 01 75834 A1 | 10/2001 |
| WO | WO 01 85085 A2 | 11/2001 |
| WO | 2002084903 A1 | 10/2002 |
| WO | 2004006768 A1 | 1/2004 |
| WO | WO 2004 093023 A2 | 10/2004 |

OTHER PUBLICATIONS

Gaymar AIRE-TWIN Operator's Manual for Alternating Pressure and Low-Air-Loss Therapy, and Mattress Replacement Systems, May 2005.
Adel 500XL Childbearing Bed, Stryker Patient Care, May 1995.
Stryker Adel 500XL Childbearing Bed Service Manual, Adel Medical Ltd. 1986.
Adel Maternity Bed Model 4700 & 5012 Operations Manual, Oct. 2003.
Advantage Stretchers Stryker Patient Handling, May 1994.
Stryker Medical Labor & Delivery Model 5000 Series, Oct. 1996.
Hausted Gemini Series, Hausted, Inc., Oct. 1993.
Stryker Adel 2100EC Childbearing Bed, Stryker Patient Care, Jan. 1994.
Office Action for Singaporean patent application serial No. 200803045.4 which is the foreign counterpart of the present application.
Partial Search Report for PCT/US2006/043290 (which corresponds to the present application U.S. Appl. No. 11/557,349), dated Mar. 14, 2007.
PCT Written Opinion of the International Searching Authority regarding PCT/US06/043290, the international counterpart of the present application that includes the same claims as the present application.
Singaporean Office Action dated Mar. 19, 2010 for Serial No. 2008/03045.4 a foreign counterpart to the present application (including Austrian Patent Office Written Opinion).
Current claims of Singapore Application No. 2008/03045.4.
Search report and written opinion of EP Application No. 06827596.5, dated May 10, 2010.
Claims of EP 06827596.5, as of May 10, 2010.

* cited by examiner

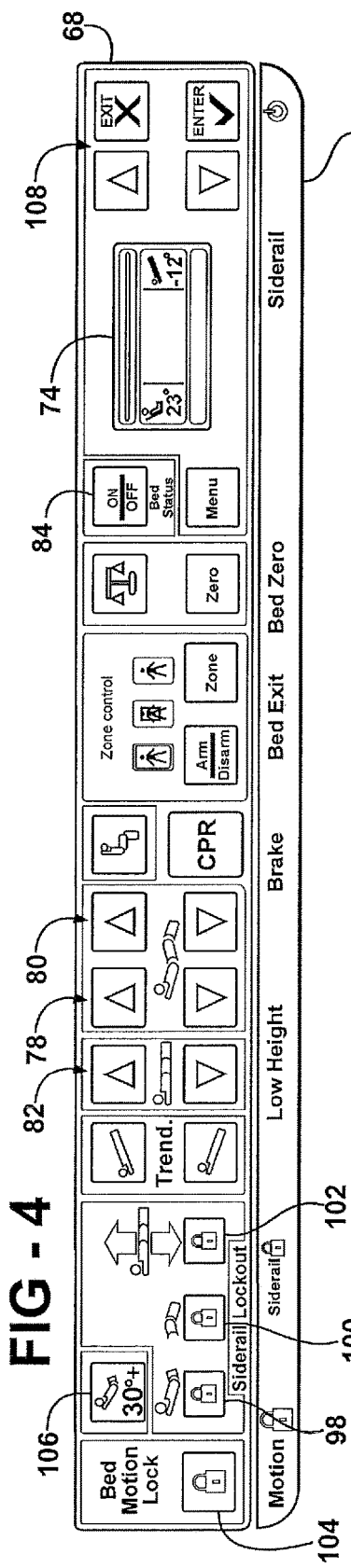
FIG - 4
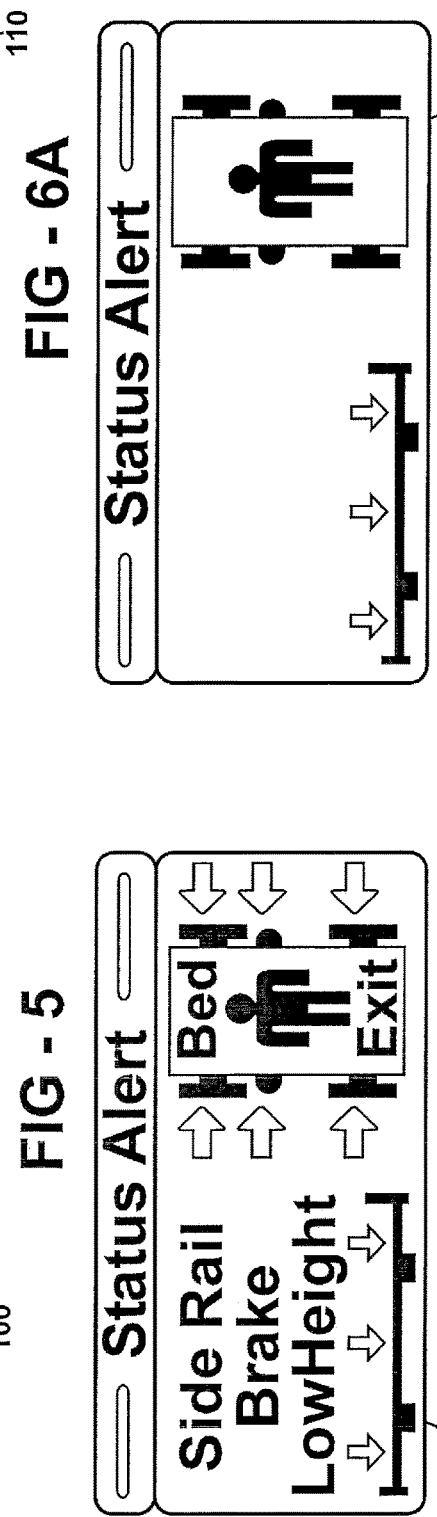
FIG - 5
FIG - 6A
FIG - 6B

PATIENT HANDLING DEVICE INCLUDING LOCAL STATUS INDICATION, ONE-TOUCH FOWLER ANGLE ADJUSTMENT, AND POWER-ON ALARM CONFIGURATION

CROSS REFERENCE TO RELATED APPLICATIONS

This application is a continuation of U.S. patent application Ser. No. 14/165,308. filed by David Terrance Becker et al. on Jan. 27, 2014, entitled PATIENT HANDLING DEVICE INCLUDING LOCAL STATUS INDICATION, ONE-TOUCH FOWLER ANGLE ADJUSTMENT, AND POWER-ON ALARM CONFIGURATION, which is a continuation of filed U.S. patent application Ser. No. 11/557, 349, filed by David Terrance Becker et al. on Nov. 7, 2006, entitled PATIENT HANDLING DEVICE INCLUDING LOCAL STATUS INDICATION, ONE-TOUCH FOWLER ANGLE ADJUSTMENT, AND POWER-ON ALARM CONFIGURATION, which claims the benefit of U.S. Provisional Patent Application Ser. No. 60/734,083 filed Nov. 7, 2005, which are hereby incorporated herein by reference in their entireties.

BACKGROUND OF THE INVENTION

1. Field of the Invention

The subject invention relates to a patient handling device such as a hospital bed and associated methods of operation.

2. Description of the Related Art

Modern patient handling devices are becoming increasingly integrated with advanced electronic devices, such as a microprocessors, communication busses, network interfaces, wireless networks, high-tech displays, and advanced sensors. These electronic devices have the potential to greatly enhance patient care. But too often, these electronic devices are complex and do not adequately address ease of use, which can be essential for patient care by accounting for the stresses of a hospital/medical environment. As a result, modern patient handling device controls and user interfaces may be difficult to operate.

One difficulty is the complexity involved in setting the desired state of the components of the patient handling device in order to produce an alarm should the components be in a non-desired state. Another difficulty is the ability to even notice when the patient handling device is alarming due to one or more components in a non-desired state. Yet another difficulty is the ability to prevent a patient from lowering a fowler of the patient handling device past prescribed angular position, yet maintaining the ability for the patient to still selectively adjust the fowler between a plurality of angular positions above the prescribed angular position. Therefore, there is a need in the art for a patient handling device that can address the difficulties described above.

SUMMARY OF THE INVENTION AND ADVANTAGES

A first aspect of the present invention provides a method of monitoring a patient handling device. The patient handling device includes a plurality of sensors sensing a plurality of features of the patient handling device and a controller in communication with the sensors. The method includes the step of receiving a control signal at the controller to initiate monitoring of the patient handling device. Sensor signals are acquired at the controller from the sensors in response to receiving the control signal. Initial sensor data is generated from the sensor signals based on the initial state of the sensors to establish a desired state of the patient handling device. The method continues with the steps of periodically acquiring the sensor signals from the sensors after generating the initial sensor data and generating current sensor data from the sensor signals based on the current state of the sensors. The current sensor data is compared to the initial sensor data and an alarm is generated in response to a substantial variation between the current sensor data and the initial sensor data.

A second aspect of the invention provides a patient handling device having a plurality of features for patient care. The patient handling device includes a frame for supporting a patient and a plurality of sensors supported by the frame for generating a plurality of sensor signals, wherein each sensor signal corresponds to one of the features of the device. A user-selectable control produces a control signal to initiate monitoring of the patient handling device. A controller is in communication with the sensors and the user-selectable control for receiving the control signal, acquiring the sensor signals from the sensors in response to receiving the control signal, and generating initial sensor data from the sensor signals based on the initial state of the sensors. The controller also periodically acquires the sensor signals from the sensors and generates current sensor data from the sensor signals based on the current state of the sensors. The controller then compares the current sensor data to the initial sensor data and alarms in response to a substantial variation between the current sensor data and the initial sensor data.

A third aspect of the invention provides a patient handling device having a plurality of features for patient care and a frame for supporting a patient. A plurality of sensors are supported by the frame, wherein each sensor senses a feature of the patient handling device and generates a sensor signal corresponding to one of the features of the patient handling device. The patient handling device further includes a controller in communication with the plurality of sensors for periodically acquiring the sensor signals from the plurality of sensors to generate current sensor data. The controller also compares the current sensor data to predetermined data. An alert lamp in communication with the controller produces light in response to a substantial variation between the current sensor data and the predetermined data. The light produced by the alert lamp is viewable outward from the frame along at least 180 degrees of a circle defined around the frame.

A fourth aspect of the invention provides a patient handling device including a frame for supporting a patient above a surface. The frame includes an upper portion which is angularly adjustable with respect to the surface. An actuator is operatively connected to the upper portion for adjusting the upper portion between a plurality of angular positions relative to the surface. An actuator control generates an actuator control signal and an angular position sensor is coupled to the frame for sensing the angular position of the upper portion with respect to the surface. The patient handling device further includes a position lock control for generating a position lock signal. A controller is in communication with the actuator control and the actuator for controlling the actuator to selectively adjust the upper portion between the plurality of angular positions. The controller is also in communication with the position lock control and the angular position sensor for preventing operation of the actuator and thereby preventing adjustment of the upper portion to at least one restricted angular position in response to the position lock signal In a fifth aspect of the invention, a method of operating a patient handling device is provided. The patient handling device includes a frame for supporting a patient above a surface. The frame includes an upper portion which is angularly adjustable with respect to the surface and an actuator for adjusting the upper portion. The method includes the step of receiving an actuator control signal to adjust the upper portion between a plurality of angular positions relative to the surface. The method also includes the step of sensing an angular position of the upper portion with respect to the surface. When a position lock signal is received, operation of the actuator is prevented, which thereby prevents adjustment of the upper portion to at least one restricted angular position.

The first and second aspects of the invention allow a user of the patient handling device to easily configure the desired state of the patient handling device. This is accomplished by simply setting the patient handling device to the desired configuration (e.g., setting angles, heights, and siderail positions) and turning the patient handling device on. The initial state of the patient handling device is recorded and the patient handling device produces an alarm when the patient handling device is no longer in this initial state.

The third aspect of the invention provides at least one alert lamp which is viewable to alert the user when any of a number of sensors indicates an alarm condition. The light produced by the alert lamp is viewable at numerous locations around the bed.

The fourth and fifth aspects of the invention provide a simple, one touch lockout that allows a patient to adjust a fowler of the patient handling device, but prevents the patient from lowering the fowler past a certain point.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 4 IS a detailed view of a footboard control panel and annunciator;

FIG. 5 is a detailed view of a display of the footboard control panel showing an example of several alarms;

FIGS. 6A and 6B are detailed views of the display of the footboard control panel showing a low height alarm;

DETAILED DESCRIPTION OF THE INVENTION

Figure 1:
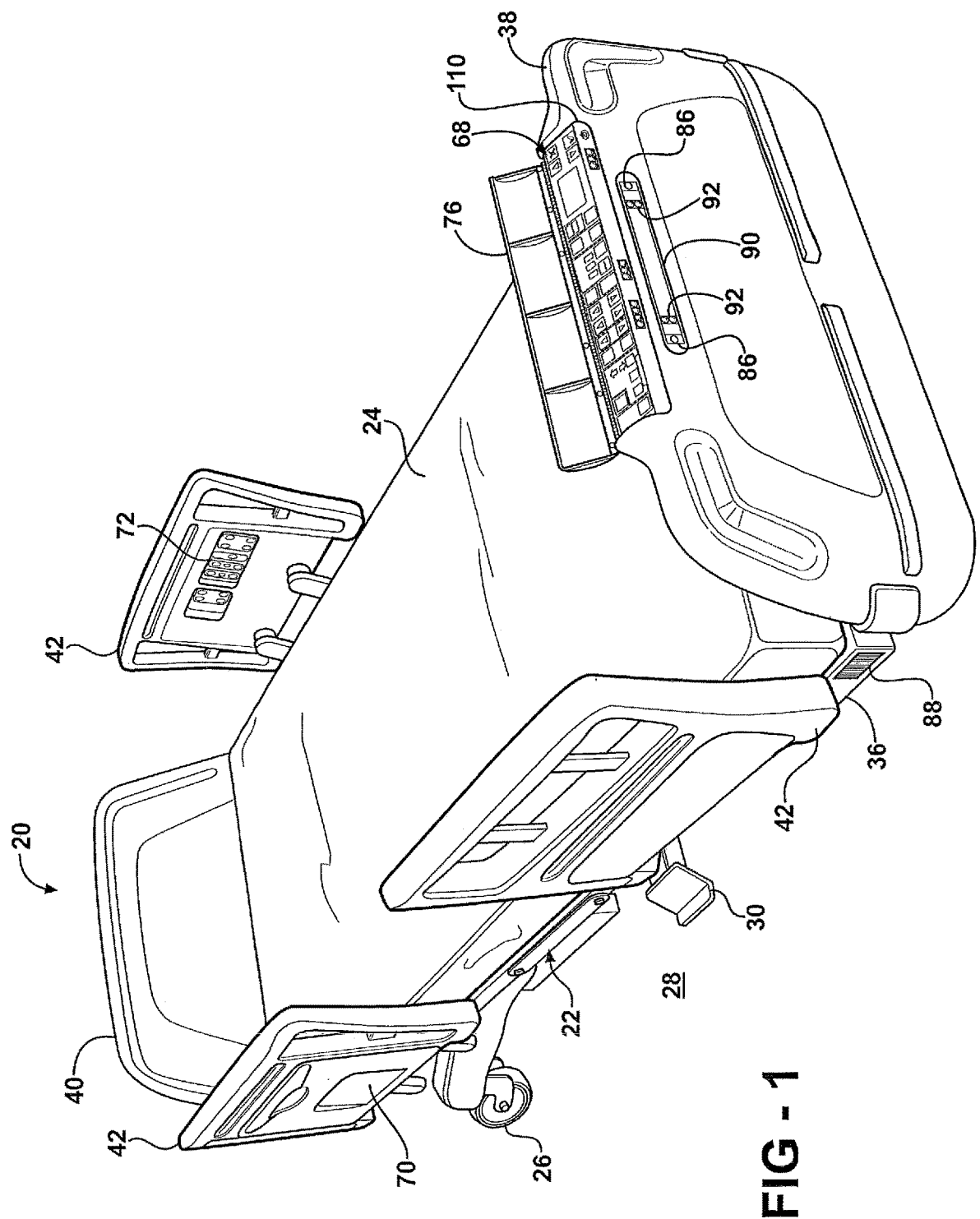
FIG. 1 is a perspective view of a patient handling device with a mattress.

Referring to the Figures, wherein like numerals indicate corresponding parts throughout the several views, a patient handling device 20 is shown in FIG. 1. Those skilled in the art realize that the patient handling device 20 of the present invention may be implemented as a gurney, stretcher, surgical table, examination table, wheel chair, ambulance cot, or other suitable device as is known to the art. Furthermore, the patient handling device 20 need not be utilized solely in a hospital, but in any suitable environment.

The patient handling device 20 includes a frame 22 for supporting a patient (not shown). A mattress 24 is preferably disposed on the frame 22 for comfortably supporting the patient. However, those skilled in the art realize that the patient handling device 20 may be implemented without the mattress 24 or with numerous alternatives for the mattress 24, such as cushions. The mattress 24 could be a therapy mattress such as that disclosed in U.S. patent application Ser. No. 11/260,452, filed Oct. 27, 2005, which is hereby incorporated by reference.

The patient handling device 20 also preferably includes a plurality of wheels 26 supporting the frame 22. The wheels 26 allow the patient handling device 20 to be easily moved along a surface 28 (i.e., the floor). Of course, the patient handling device 20 may be implemented without the wheels 26, such that the patient handling device 20 is relatively stationary. When implemented with the wheels 26, the patient handling device 20 preferably includes a brake for immobilizing at least one of the wheels 26 and more preferably immobilizing all of the wheels 26. The brake is applied via a brake pedal 30. In alternative embodiments, the brake may be applied utilize a handle, button, or other suitable activation technique. Braking systems employed on patient handling devices are well known in the art and any suitable system may be employed here, thus the braking system is not described in detail.

Figure 2:
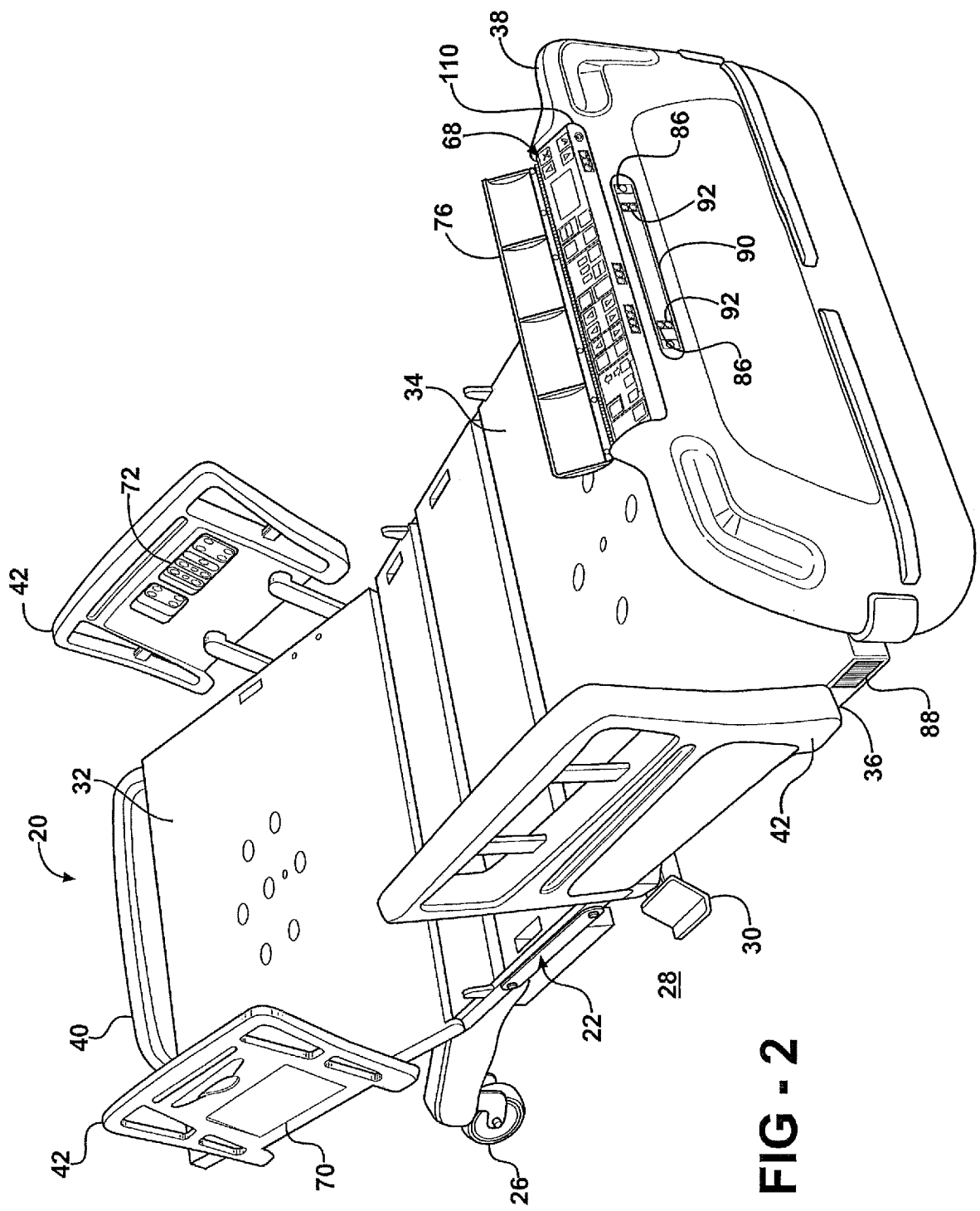
FIG. 2 is a perspective view of the patient handling device with the mattress removed to illustrate the upper portion in an inclined position.

Referring to FIG. 2, the frame 22 includes an upper portion 32 and a lower portion 34. The upper portion 32 is often referred to as a "fowler portion" or simply a "fowler". The upper and lower portions 32, 34 are angularly adjustable with respect to the surface 28 between a plurality of angular positions. The another way, the upper and lower portions 32, 34 may be adjusted such that they are non-parallel with the surface 28. This allows the patient to be positioned in a variety of configurations as are well known to those skilled in the art. The angular position of the upper portion 32 with respect to the surface 28 is commonly referred to as a "fowler angle" or "fowler position".

The frame 22 defines two sides 36 running lengthwise with the arms and legs of a patient lying in the patient handling device 20 and two ends (not labeled) transverse to the sides 36. A footboard 38 is disposed transverse to the sides 36 and adjacent to one of the ends. Likewise, a headboard 40 may be disposed transverse to the sides 36 and adjacent to the other end of the frame 22. Obviously, the footboard 38 is typically disposed near the feet of a patient lying on the patient handling device 20 while the headboard 40 is disposed near the head of the patient.

The patient handling device 20 also includes at least one siderail 42 disposed adjacent one of the sides 36 of the frame 22. The siderail 42 is moveable between an up position and a down position. In the up position, the siderail 42 prevents the patient from accidentally rolling off the patient handling device 20 or easily exiting the patient handling device 20. It is preferred that the siderail 42 include a locking mechanism (not shown) to lock the siderail 42 in the up position, such that it may not be easily lowered by the patient. In the preferred embodiment, the at least one siderail is implemented as a plurality of siderails, and more preferably as four siderails: two adjacent the upper portion 32 with one on each side 36 of the frame 22 and two adjacent the lower portion 34 with one on each side 36 of the frame 22. In FIGS. 1 and 2, three of the siderails 42 are shown in the up position and one (not shown) is in the down position.

Figure 3:
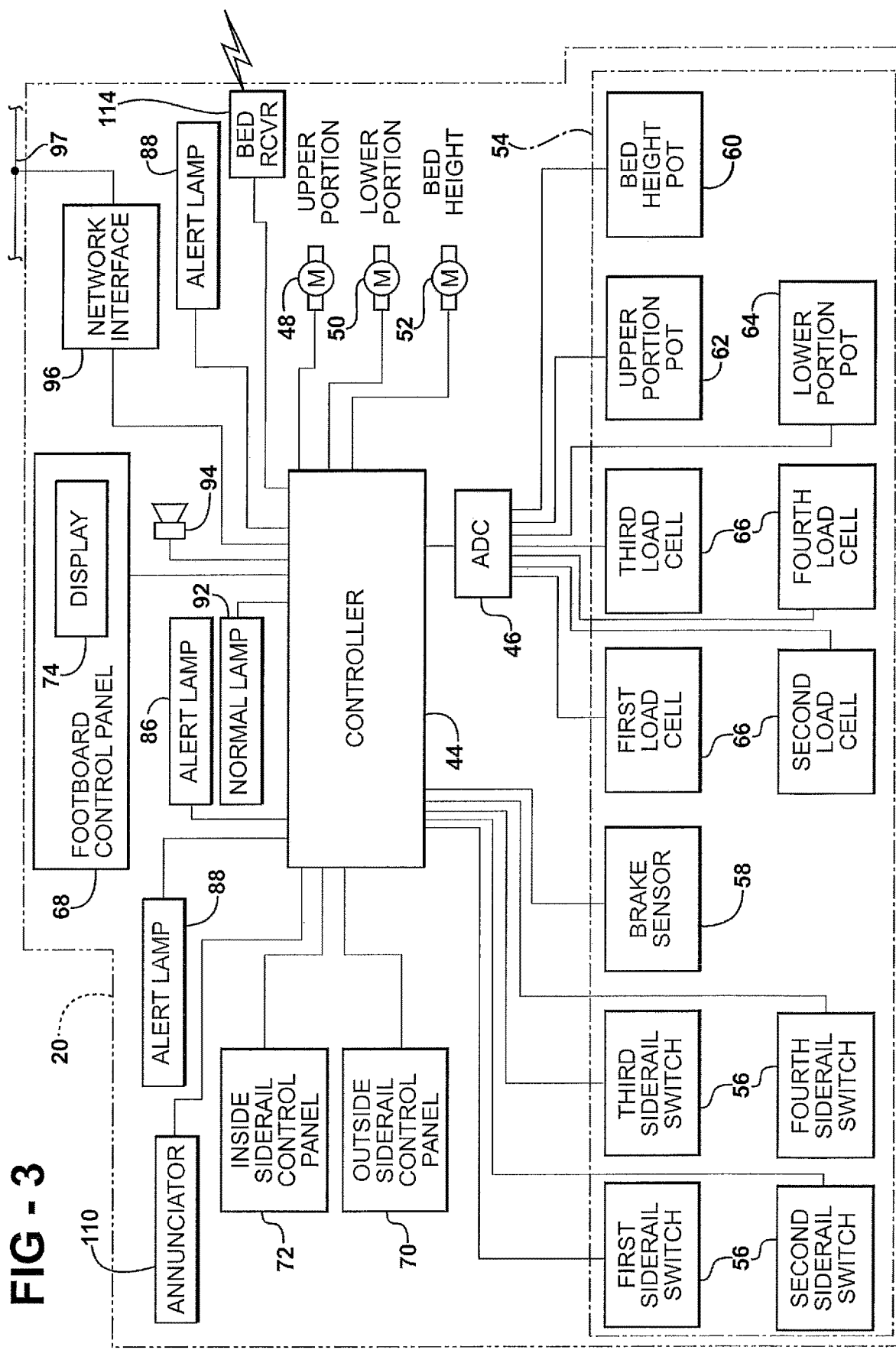
FIG. 3 is a schematic block diagram of the various electrical and electronic components of the patient handling device.

Referring now to FIG. 3, the patient handling device 20 includes a controller 44 for controlling operation of the patient handling device 20 and monitoring various features of the patient handling device 20. The controller 44 is preferably a microprocessor-based device, such as a microcontroller. However, those skilled in the art realize that other suitable implementations may be employed for the controller 44. The patient handling device 20 also includes a variety of electrical and electronic components (not shown) interfaced with or integrated into the controller 44 for enabling operation of the controller 44 and communication with the controller 44. These components may include, but are not limited to, power supplies, communication interface circuits, networking circuits, amplifiers, multiplexers, logic gates, resistors, capacitors, inductors, and diodes. At least one analog-to-digital converter 46 (ADC) is electrically connected to the controller 44 to convert analog signals from variable voltage/current devices to digital signals which are usable by the controller 44. The at least one ADC 46 may be separate (i.e., stand-alone) from the controller 44 and/or integrated within the controller 44. Furthermore, the patient handling device 20 may also include a plurality of distributed nodes (not shown) electrically connected to the controller 44 and various electrical/electronic devices as described herein. The distributed nodes facilitate communication between the devices and the controller 44 while reducing overall wiring costs and complexity.

The patient handling device 20 includes an upper portion actuator 48 operatively connected to the upper portion 32. The upper portion actuator 48 moves the upper portion 32 to adjust the upper portion 32 between a plurality of angular positions. The upper portion actuator 48 is in communication with the controller 44 to receive control signals from the controller 44. The upper portion actuator 48 is preferably a bi-directional motor such that the upper portion actuator 48 can increase and decrease the angular position of the upper portion 32 with respect to a horizontal surface 28 such as the floor upon which the patient handling device 20 is supported. The patient handling device 20 also includes a lower portion actuator 50 operatively connected to the lower portion 34 for moving the lower portion 34 to adjust the lower portion 34 between a plurality of angular positions. The lower portion actuator 50 is electrically connected to the controller 44 and is preferably a bi-directional motor and operates similarly to the upper portion actuator 48 described above. The patient handling device 20 also includes a lifting mechanism 52 operatively connected to the frame 22 for lifting and lowering the frame 22 with respect to the surface 28. The lifting mechanism 52 is electrically connected to the controller 44 and preferably includes a bi-directional motor. Of course, those skilled in the art realize that the patient handling device 20 may include other actuators for operating features of the patient handling device 20. The actuators 48, 50 and lifting mechanism 52 are well known to those skilled in the art and any suitable actuator 48, 50 or lifting mechanism 52 may be implemented; therefore, the actuators 48, 50 and lifting mechanism 52 are not described in further detail.

A plurality of sensors 54 are supported by the patient handling device 20 with each sensor 54 being associated with the various features of the patient handling device 20. Each sensor 54 senses at least one feature of the patient handling device 20 and generates a sensor signal corresponding to that feature of the patient handling device 20. These sensors 54 include, but are not limited to:

at least one siderail switch 56 for sensing the position of each siderail 42, specifically, whether each siderail 42 is in the up position;
   a brake sensor 58 for sensing the activation of the brake;
   a height sensor 60 for sensing the height of the frame 22 with respect to the surface 28.
   an upper portion potentiometer 62 for sensing an angular position of the upper portion 32 with respect to the surface 28;
   a lower portion potentiometer 64 for sensing an angular position of the lower portion 34 with respect to the surface 28;
   at least one load cell 66, and preferably four load cells 66, for sensing the weight, presence, and/or position of the patient on the patient handling device 20; and
   an arm/disarm signal from a bed exit system.

Those skilled in the art will realize numerous techniques for implementing the sensors 54 with the patient handling device 20. For example, in the preferred embodiment, the siderail switches 56 are implemented as mechanical rocker-type switches. However, the siderail switches 56 may alternatively be implemented as inductive or capacitive sensing proximity switches, photosensitive detectors, etc. Furthermore, those skilled in the art will realize that additional sensors that may be utilized to monitor a feature of the patient handling device 20.

The bed exit system detects patient exit from the patient handling device 20 and/or detects a position of the patient on the patient handling device 20. Such a bed exit system is described in U.S. Pat. No. 5,276,432, which is hereby incorporated by reference. The bed exit system is preferably incorporated as one or more software routines in the controller 44 and utilizes the preferred four load cells 66 as described above. The load cells 66, via the bed exit system, may be used to track the patient's center of gravity. By knowing the patient's center of gravity, pressure ulcer management can be performed by knowing that the patient hasn't moved or turned. Furthermore, the load cells 66, via the bed exit system, may be utilized to predict a bed exit before it occurs.

Referring again to FIG. 1, the patient handling device 20 also preferably includes several control panels 68, 70, 72 in communication with the controller 44. In the preferred embodiment, the patient handling device 20 includes a footboard control panel 68 disposed in the footboard 38 of the patient handling device 20. The footboard control panel 68, as shown in detail in FIG. 4, includes a plurality of membrane-style pushbuttons for controlling various features of the patient handling device 20. Of course, the footboard control panel 68 may use different styles of pushbuttons, switches, or knobs as is well known to those skilled in the art. The footboard control panel 68 also includes a display 74 for displaying information regarding the patient handling device 20 to a user (e.g., nurse, doctor, technician, etc.). The display 74 in the preferred embodiment is a back-lit liquid crystal-type device, however, other types of displays 74, including touch-screen displays 74 for accepting user input, are known to those skilled in the art. A cover 76 is pivotally hinged to the footboard 38 adjacent to the footboard control panel 68 for concealing and protecting the footboard control panel 68 when closed. The cover 76 may include a window (not shown) to allow viewing of the display 74 when the cover 76 is closed.

Figure 10:
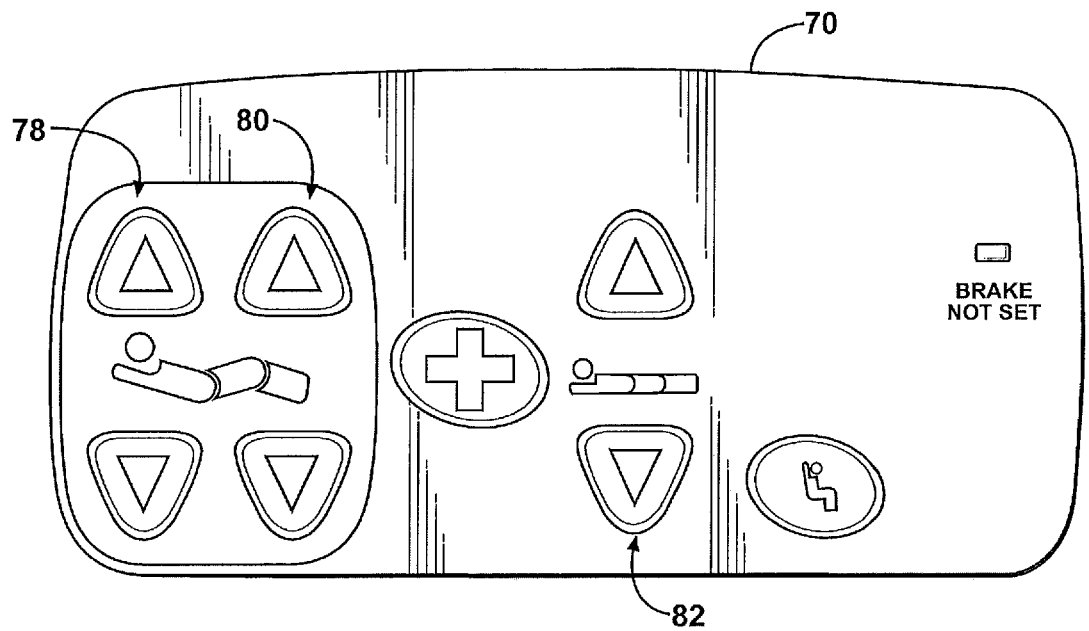
FIG. 10 is a detailed view of an outside siderail control panel.
Figure 11:
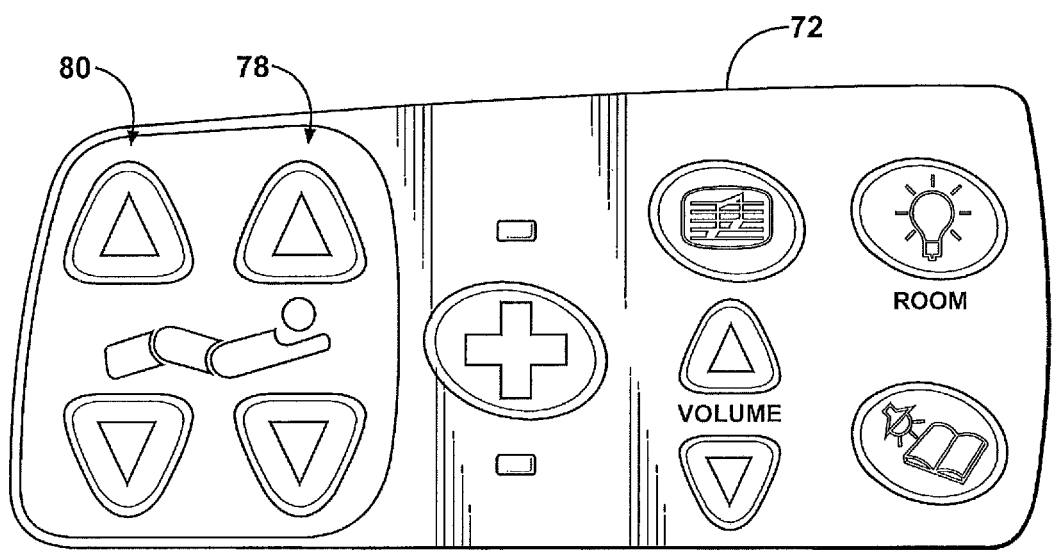
FIG. 11 is a detailed view of an inside siderail control panel.

The patient handling device 20 also preferably includes at least one outside siderail control panel 70, shown in detail in FIG. 10, and at least one inside siderail control panel 72, shown in detail in FIG. 11. The inside siderail control panel 72 is disposed on the inside (i.e., close to the patient) of at least one of the siderails 42 to allow convenient control of the patient handling device 20 and an interface to other off bed features (e.g., television control, nurse call, etc.). The outside siderail control panel 70 is disposed on the outside (i.e., away from the patient) of at least one of the siderails to allow convenient control of the patient handling device 20 by users other than the patient. The siderail control panels 70, 72 preferably include membrane-style pushbuttons, but other alternatives are known to those skilled in the art.

The patient handling device 20 includes an upper portion control 78, a lower portion control 80, and a height control 82, each control electrically connected to the controller 44. Each of these controls 78, 80, 82 is preferably implemented as a pair of membrane-style pushbuttons (one for up and one for down). In the preferred embodiment, the upper and lower portion controls 78, 80 are disposed on each of the control panels 68, 70, 72 while the height control 82 is disposed on the outside siderail control panel 70 and the footboard control panel 68, i.e., not on the inside siderail control panel 72. The upper portion control 78 generates an upper portion control signal, the lower portion control 80 generates a lower portion control signal, and the height control 82 generates a height control signal. Each of these control signals is communicated to the controller 44. The controller 44 typically responds to each control signal by controlling the actuator corresponding to the control signal in the appropriate direction. A patient or user of the patient handling device 20 can then use the controls 78, 80, 82 to selectively adjust the height, upper portion angular position, and/or lower portion angular position of the patient handling device 20.

The patient handling device 20 includes a user-selectable control for producing a control signal. In the preferred embodiment, the user-selectable control is a power button 84, preferably as part of the footboard control panel 68, as shown in FIG. 4. However, other controls for producing the control signal and other locations for the power button 84 are also acceptable. The power button 84 produces the control signal, which is sent to the controller 44 to initiate monitoring of the patient handling device 20. In the preferred embodiment, the power button 84 also controls the flow of power to the patient handling device 20. Furthermore, the power button 84 cannot be activated (i.e., power will not flow to the patient handling device 20) unless the brake has been set to immobilize the patient handling device 20.

The controller 44 receives the control signal and begins to initiate the monitoring of the patient handling device 20. Specifically, in response to receiving the control signal, the controller 44 acquires the sensor signal from each of the sensors 54 that is to be monitored. The controller 44 generates initial sensor data based on the initially acquired sensor signals. This initial sensor data then becomes the "setpoint" and is stored in a memory of the controller 44, thus establishing a desired state of the patient handling device. For example, if the sensors 54 to be monitored are the four siderail switches 56, the brake sensor 58, and the load cells 66, then the position of each siderail 42 and the brake and the weight measured by the load cells 66 are stored in the memory. If the sensors 54 to be monitored are the four siderail switches 56, the brake sensor 58, and the arm/disarm signal from the bed exit system, then the position of each siderail 42 and the brake and the current configuration of the arm/disarm signal (e.g., armed or disarmed) are stored in the memory. Thus, the initial sensor data is based on the position of the components being monitored when the power button 84 is depressed.

After generating the initial sensor data, the controller 44 then will periodically acquire the sensor signal from each of the monitored sensors 54 to generate current sensor data. This current sensor data is then compared to the initial sensor data. An alarm may be then issued in response to a substantial variation between the current sensor 54 data and the initial sensor data. This variation indicates a change from the desired state to an undesired state. Of course, the amount of variation between the current and initial sensor data that results in triggering the alarm may be adjusted, depending on the nature of the data. For example, a variation of a few pounds in the weight of the patient (between initial and current sensor data) need not trigger the alarm, but a variation of fifty pounds could. Furthermore, the step of periodically acquiring the sensor signals may be described as the controller 44 routinely examining the sensor signals to determine the current state of the sensors 54. Alternatively, the step of periodically acquiring the sensor signals may be described as being immediately triggered by a state change, such as, but not limited to, the presence of an interrupt signal at the controller 44.

Alternative methods to issuing the alarm are contemplated within the scope of the invention. In one method, the current sensor data is compared to predetermined data. This predetermined data may be set by the manufacturer of the patient handling device 20 or may be set by the user. In an embodiment in which the predetermined data is set by the user, configuration controls are provided as part of the footboard control panel 68. Those skilled in the art realize that the initial sensor data may be considered to be the predetermined data since the initial sensor data is set (i.e., predetermined) by the user's act of turning the patient handling device 20 on via the power button 84.

The alarm may be conveyed in several forms. In one instance, the alarm may be conveyed by activating an alert lamp which produces light. Referring to FIGS. 1 and 2, in the preferred embodiment, the patient handling device 20 includes a plurality of alert lamps: at least one footboard alert lamp 86 and a pair of side alert lamps 88. The footboard alert lamp 86 is coupled to the footboard 38 and disposed in a footboard lamp housing 90 located below the footboard control panel 68.

One side alert lamp 88 is disposed on one side 36 of the patient handling device 20 while the other side alert lamp 88 is disposed on the other side 36 of the patient handling device 20. The alert lamps 86, 88 are positioned such that the light produced by the alert lamp is viewable outward from the patient handling device 20 along at least 180 degrees of a circle defined around the patient handling device 20 and more preferably viewable at least 270 degrees of the circle defined by the patient handling device 20. Since the headboard 40 of the patient handling device 20 is traditionally positioned against a wall, the light produced by the alert lamps 86, 88 is viewable no matter where a user is around the patient handling device 20. Furthermore, alert lamps may be positioned such that light is viewable at any point (i.e., 360 degrees) around the patient handling device 20.

Preferably, the alert lamps 86, 88 are light emitting diodes (LEDs) such that replacement of the alert lamps 86, 88 is a rarity. It is also preferred that the alert lamps 86, 88 produce an amber (or yellow) colored light. Light having an amber color typically has a wavelength in the range of 577 to 597 nanometers. Furthermore, it is preferred that the alert lamp flash on and off, to emphasize the alarm condition. Those skilled in the art will realize other locations, configurations, colors, and wavelengths for the alert lamps 86, 88. The alert lamps 86, 88 are deactivated, i.e., turned off, when there is no substantial variation between the current sensor data and the predetermined data (or initial sensor data).

To deactivate the alarm and the alert lamps 86, 88, a user may simply correct the problem (e.g., raise a siderail that was lowered). Alternatively, deactivating the alert lamps 86, 88 may be accomplished by simply turning off power to the patient handling device 20 by pressing the power button 84 and then turning power back on, by again pressing the power button 84. When the patient handling device 20 is restarted, the initial sensor data will be set to the current (and desired) state.

The patient handling device 20 may also include a normal lamp 92 which is activated (i.e., illuminated) when there is no substantial variation between the current sensor data and the predetermined data (or initial sensor data). The another way, the normal lamp 92 is illuminated when there is no alarm. The normal lamp 92 is also preferably disposed within the footboard lamp housing 90. The normal lamp 92 produces a light having a wavelength different from the wavelength of the light produced by the alert lamp. Preferably, the normal lamp 92 is at least one LED that produces a green colored light. Those skilled in the art realize that green color light has a wavelength in the range of 492 to 577 nanometers. The normal lamp 92 is deactivated, i.e., turned off, when there is a substantial variation between the current sensor data and the predetermined data (or initial sensor data), i.e., when the patient handling device 20 is in the undesired state.

Thus, in the preferred embodiment, it is easy for a user (e.g., nurse, doctor, orderly, etc.) to quickly determine if there is a problem with the patient handling device 20 that needs to be addressed. The user need simply notice whether the patient handling device 20 is producing a green light or a flashing amber light.

In another instance, the alarm may be conveyed to a user by sounding an audible signal. The patient handling device 20 may include a speaker 94 in communication with the controller 44 for sounding this audible signal.

In yet another instance, the alarm may be conveyed by transmitting alarm data to a remote computer 95, external from the patient handling device 20. The controller 44 of the patient handling device 20 is in communication with a network interface 96. The network interface 96 may then communicate the alarm data (as well as other data) to the remote computer 95 over a network 97. Those skilled in the art realize that the network 97 may be a hardwired network (e.g., Ethernet) or a wireless network (e.g., WiFi., cellular telephone, GSM, Bluetooth, etc.).

The alarm my also be conveyed by transmitting a nurse call signal to a nurse call system. Nurse call systems are well known to those skilled in the art, but typically lack functionality for detailed data handling. Rather, nurse call systems typically provide a simple on/off signal to alert the user (e.g., a nurse) to a problem.

The patient handling device 20 of the present invention also provides functionality for limiting (or locking out) operation of the patient handling device 20. The footboard control panel 68 includes an upper portion lockout control 98, a lower portion lockout control 100, a height lockout control 102, and a motion lockout control 104. Each of these lockout controls 98, 100, 102, 104 is electrically connected to the controller 44 and sends a corresponding lockout control signal to the controller 44 when activated. For example, when the lower portion lockout control 98 is activated, the lower portion actuator 50 will not function when the lower portion controls 80 on the siderails 42 and/or the footboard control panel 68 are depressed. The same reasoning extends to the upper portion lockout control 100, the height lockout control 102, and the motion lockout control 104.

The patient handling device 20 of the present invention also provides a position lock control 106. The position lock control 106 is preferably a membrane-style pushbutton located in the footboard control panel 68 and electrically connected to the controller 44. The position lock control 106 generates a position lock signal which is received by the controller 44. The activation of the position lock control 106 in the preferred embodiment provides several results. First, the lower portion actuator 48 is actuated to position the lower portion to a horizontal position (i.e., parallel with the surface 28). Next, the upper portion actuator 48 is actuated to position the upper portion 32 outside of a restricted range of angular positions of the upper portion 32. In the preferred embodiment, this restricted range is between 0 and 30 degrees with respect to the surface 28. However, different ranges of angular positions may also be utilized. For example, in one alternative embodiment, the restricted range may be between 0 and 45 degrees. In another alternative embodiment, the restricted range may be any angular position greater than 45 degrees. If the upper portion 32 is already positioned outside the restricted range of angular positions, then no actuation takes place. The controller 44 receives feedback (i.e., the current position of the upper portion 32) from the upper position sensor 54.

Finally, activation of the position lock control 106 results in preventing the operation of the upper portion actuator 48 utilizing the upper portion control 78 into the restricted range of angular positions. Thus, in the preferred embodiment, the patient (or other user) is not able to lower the upper portion 32 under 30 degrees utilizing the pushbuttons of the upper portion control 78. This allows a simple and convenient technique for a user to place the patient in an inclined position and keep the patient in that position. In some embodiments, however, even when the position lock control 106 is actuated, the upper portion 32 can be adjusted through a plurality of permitted angular positions that fall outside the restricted range of angular positions, such as those positions above 30 degrees with respect to the surface 28. Those skilled in the art realize that certain medical conditions necessitate positioning patients in these permitted positions for extended periods of time. Those skilled in the art realize other restricted range of angular positions that have clinical or operational significance. Two examples of restricted ranges of angular positions are related to the commonly known Trendelenberg position (where the patient's feet are disposed higher than their head) and the knee gatch position. Of course, if CPR is to be initiated, a CPR button allows immediate movement of the upper and lower portions of the bed to a fully horizontal position.

In the preferred embodiment described above, the position lock control 106 restricted the range of angular positions of the upper portion 32. In other embodiments, however, the position lock control 106 may alternatively restrict the range of angular positions of other portions of the patient handling device 20, such as, but not limited to, the lower portion 34.

The patient handling device 20 also includes an annunciator 110 for quickly alerting the user to status conditions of the patient handling device 20. The annunciator 110 is preferably located adjacent to and below the footboard control panel 68, however other locations may also be acceptable. The annunciator 110 includes annunciator lamps (not shown) electrically connected to the controller 44. A cover plate is affixed over the annunciator lamps, such that messages are illuminated when appropriate. These messages may include, but are not limited to:
Motion Lockout Set
Siderail Lockout Set
Low Height
Brake Set
Bed Exit Alarm
Zero Weight Alarm
Siderail Alarm
Power On One advantageous feature of the annunciator 110 is that it remains visible to the user, even when the cover 76 of the footboard control panel 68 is closed.

Figure 7A:
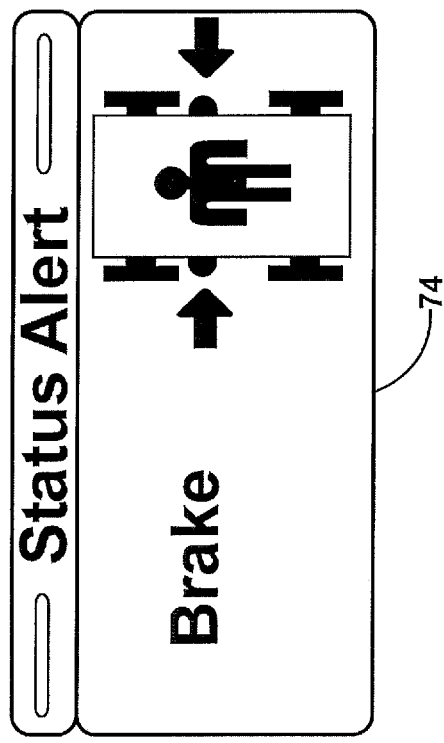
FIGS. 7A and 7B are detailed views of the display of the footboard control panel showing a brake alarm.
Figure 8A:
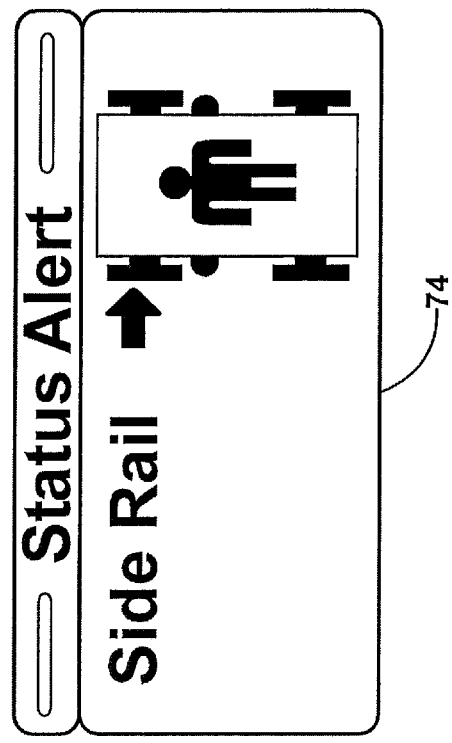
FIGS. 8A and 8B are detailed views of the display of the footboard control panel showing a siderail alarm.
Figure 7B:
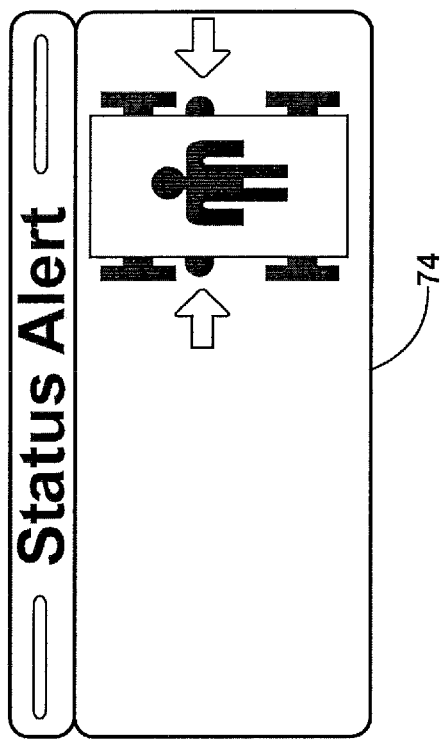
Figure 8B:
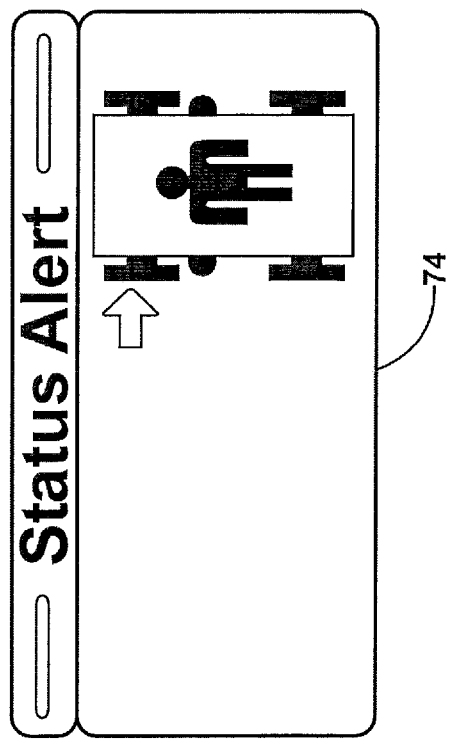
Figure 9A:
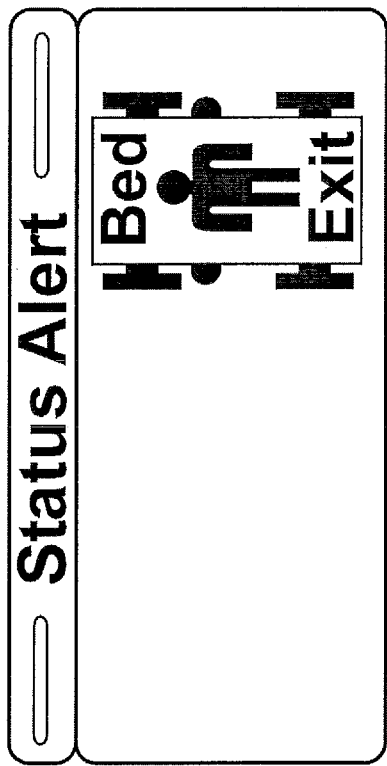
FIGS. 9A and 9B are detailed views of the display of the footboard control panel showing a bed exit alarm.
Figure 9B:
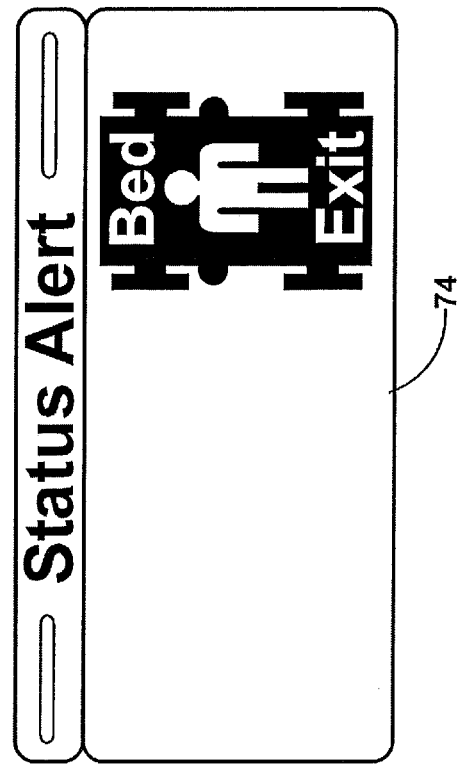

The display 74 of the footboard control panel 68 is used as an interface between a user of the patient handling device 20 and the controller 44. As shown in FIG. 4, the display may provide information to the user, such as the upper portion angular position and the lower portion angular position. Referring to FIG. 5, the display 74 may provide a graphical representation and/or a schematic map of the patient handling device 20 to indicate which component is triggering an alarm. The triggering component may be blinking or otherwise indicated as is known to those skilled in the art. For example, FIGS. 6A and 6B will alternate on the display 74, creating a blinking effect to inform the user that the height of the patient handling device 20 is low (i.e., lower than the desired state). FIGS. 7A and 7B will alternate on the display 74 to show the user that the brake is no longer set. Likewise, FIGS. 8A and 8B show that one of the siderails 42 is out of position and FIGS. 9A and 9B indicate that a bed exit alarm is tripped.

Figure 12:
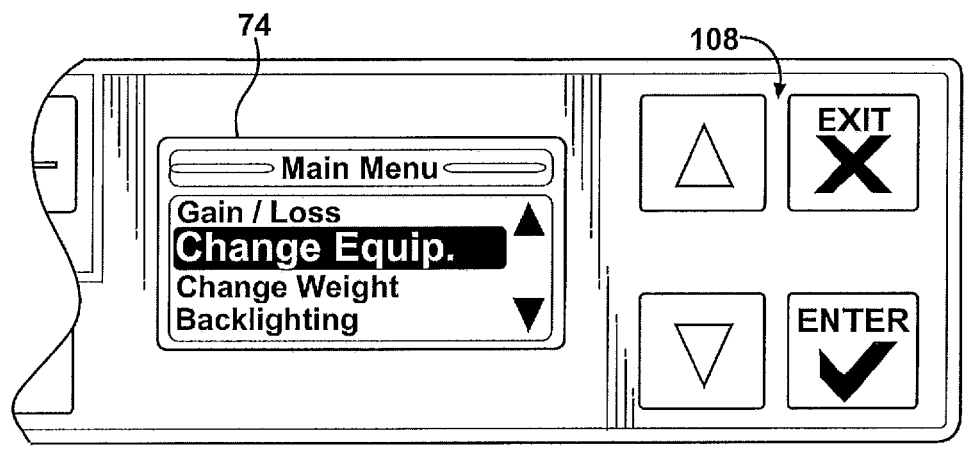
FIG. 12 is a detailed view of the display of the footboard control panel showing a menu.
Figure 13:
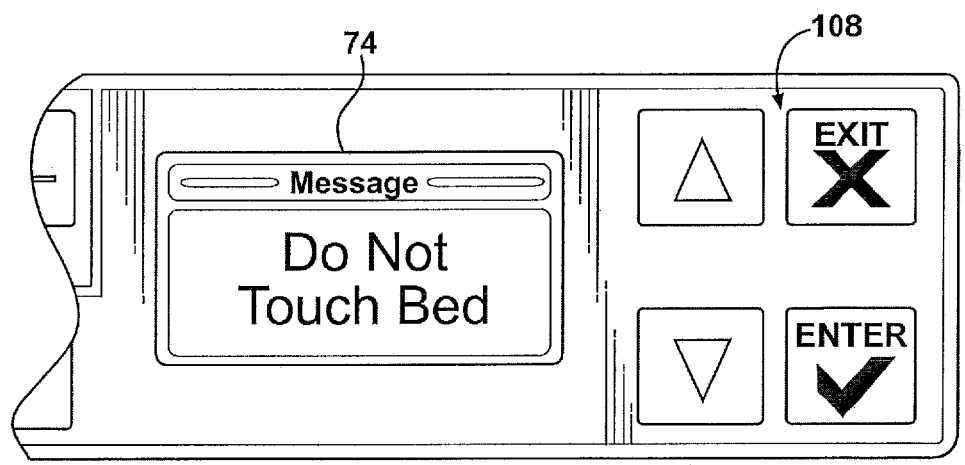
FIG. 13 is a detailed view of the display of the footboard control panel showing an instructional message.

As shown in FIG. 12, the display may provide a menu from which the user can configure features of the patient handling device, by utilizing user interface controls 108 located on the footboard control panel 68. The display 74 can also convey non-alarm messages to the user, such as in FIG. 13, instructing the user not to touch the bed (e.g., while the patient is weighed).

Figure 14:
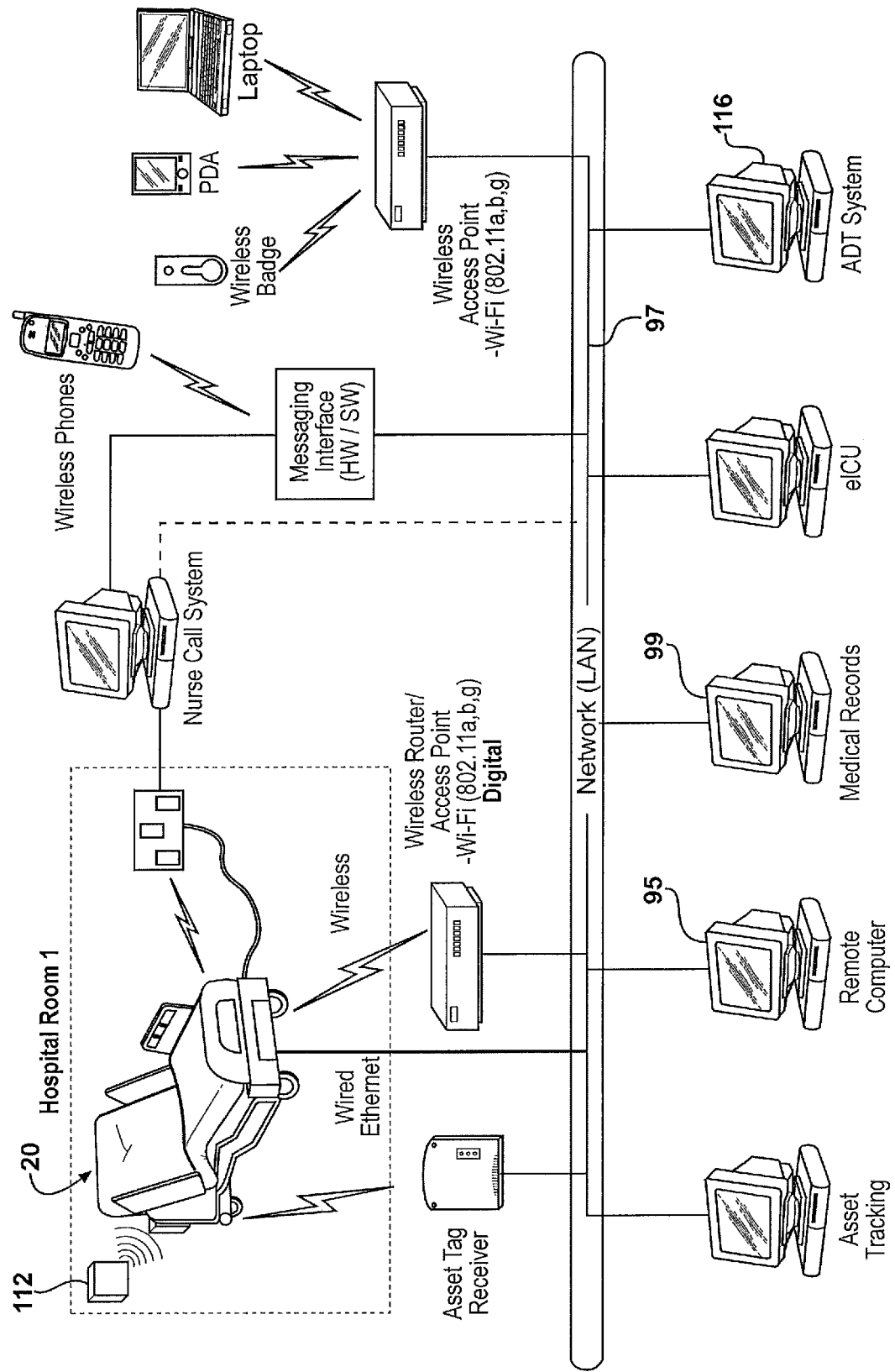
FIG. 14 is a schematic view of a healthcare facility with a network and a patient handling device bay ID system.

Referring now to FIG. 14, the patient handling device 20 of the present invention may be a part of a location detection system (not labeled). The location detection system locates patient handling devices 20 in a facility such as a hospital. Such a location detection system is described in U.S. patent application Ser. No. 11/277,838, filed on Mar. 29, 2006, which is hereby incorporated by reference.

The location detection system includes a locator 112 mounted at each bay location in each room of the hospital. The locator 112 is programmed with a location ID to transmit to the patient handling device 20 once the patient handling device 20 has "docked" with the locator 112. The locator 112 could be mounted on the ceiling, wall, floor, or any location that permits the locator 112 to carry out its intended function.

Figure 15:
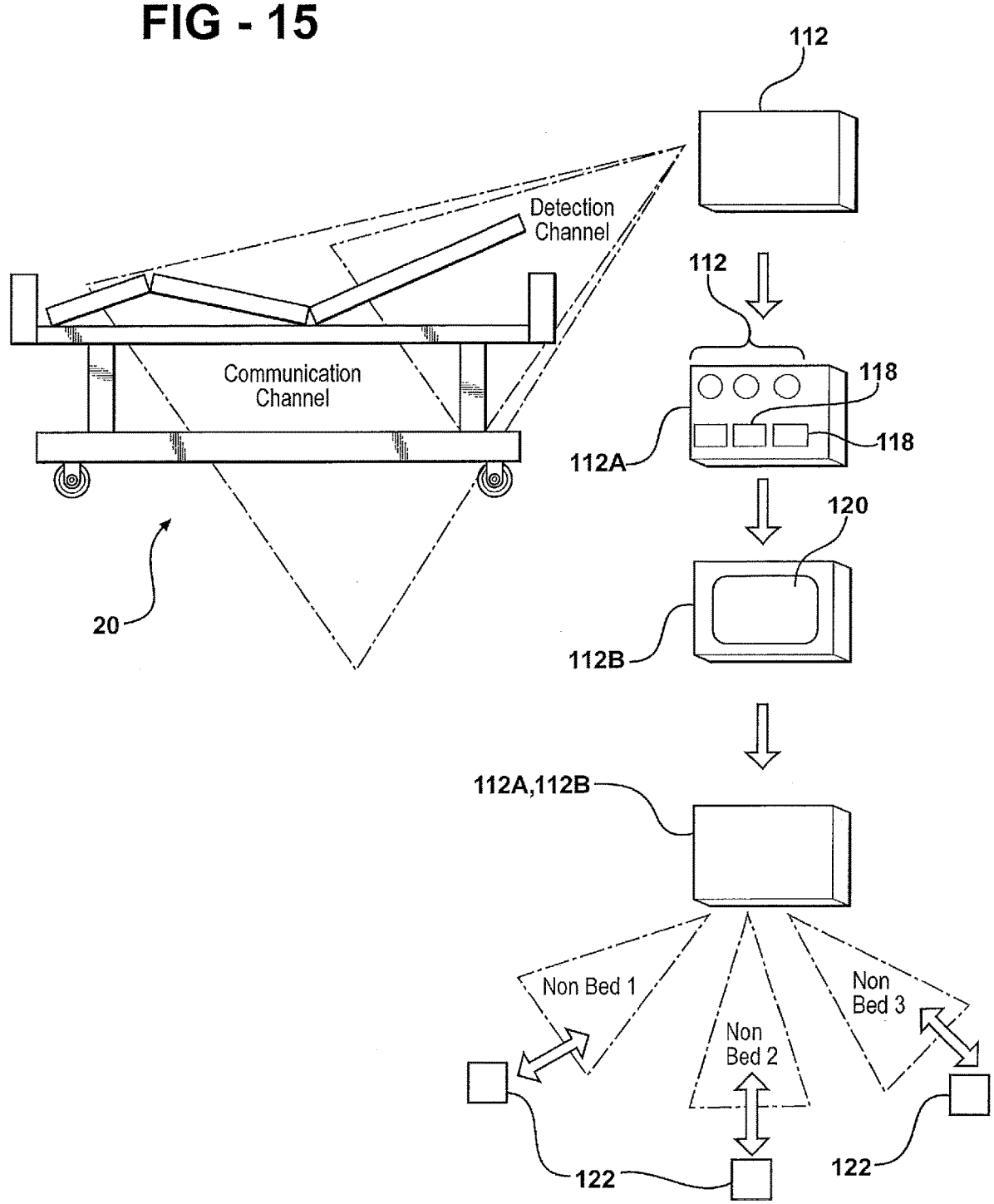
FIG. 15 is a schematic view of alternative room modules in the patient handling device bay ID system illustrating their communication with the patient handling device and non-patient handling device devices.

Referring to FIG. 15, the locator 112 could also include additional features to provide an intelligent room module 112A. For instance, the intelligent room module 112A may include interface buttons 118 for operator selection that correspond to the patient handling device 20 or room being clean, dirty, empty, occupied, ready for occupancy, etc. An alternative intelligent room module 112B may also include a graphic display 120 such as a touch-screen display with multiple nested user screens to access or transmit patient data, patient handling device data, or room data. The intelligent room module 112A, 112B may transmit this information, e.g., clean/dirty, etc., directly or indirectly to the hospital network 97 using wired and/or wireless communication paths. Communication can occur from the intelligent room modules 112A, 112B directly to the hospital network 97, from the intelligent room modules 112A, 112B to other patient handling devices and then to the hospital network 97 or to more than one available hospital network, or directly from the intelligent room modules 112A, 112B to the computer 95 or to more than one computer 95. The intelligent room modules 112A, 112B may also be configured as access points between the patient handling devices 20 and multiple non-bed devices 122 such as patient monitoring devices, patient treatment devices, diagnostic devices, and the like, or the intelligent room modules 112A, 112B may be configured as access points between the hospital network 12 and the non-bed devices 122.

As stated above, data may be transmitted to the remote computer 95 from the patient handling device 20 via the network 97. This data may include, but is not limited to, any data collected by the controller 44 of the patient handling device 20, alarm data, location ID data, and non-bed device data from non-bed devices 122 in communication with the patient handling device 20. This data may also be utilized by other systems present on the network 97. For instance, the data may be automatically transmitted to an electronic medical record system 99. Furthermore, the controller 44 of the patient handling device 20 may receive commands initiated at the remote computer 95.

Figure 16:
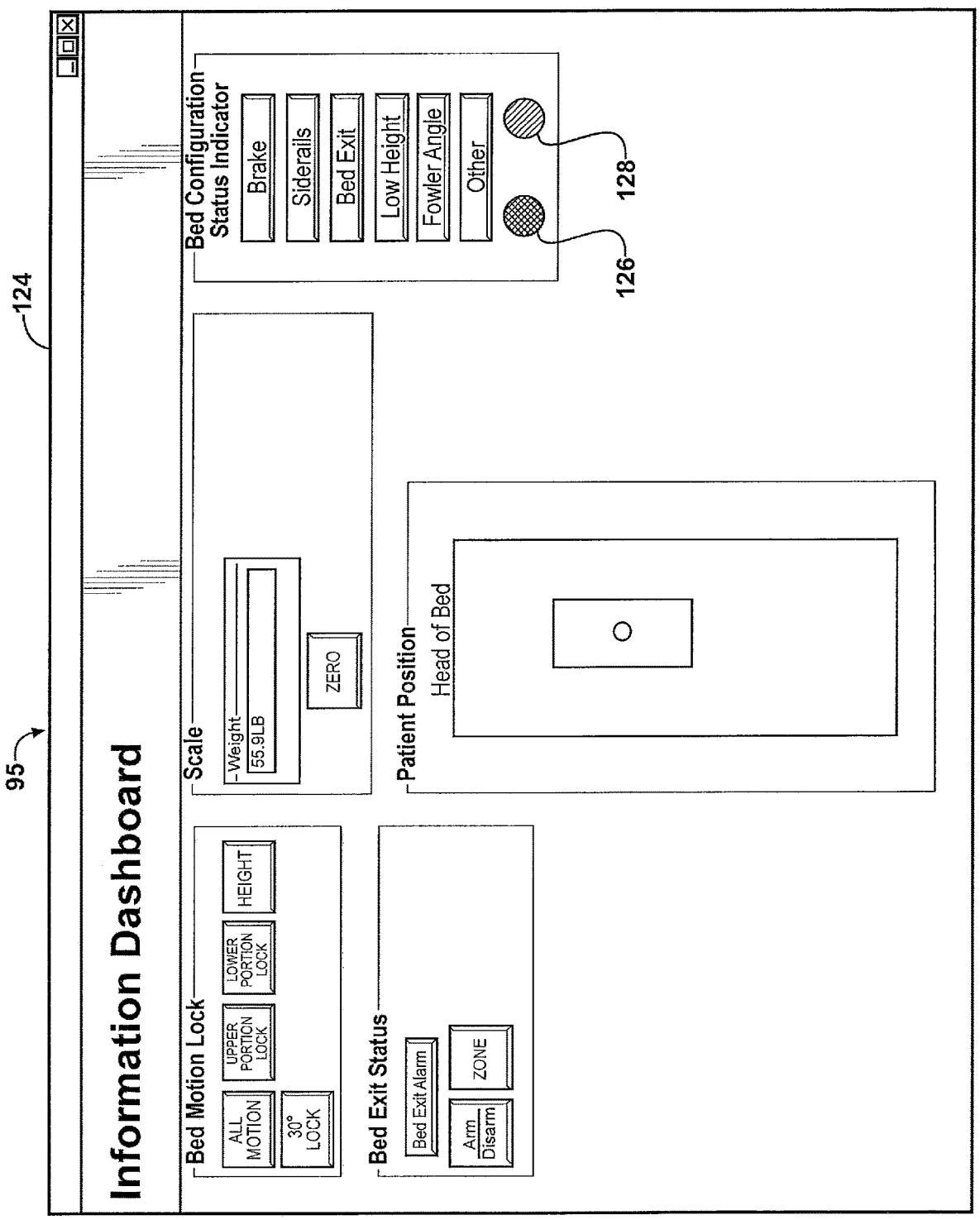
FIG. 16 is a display representation at a remote computer illustrating a user interface of the present invention.

Referring to FIG. 16, one possible configuration of a display 124 at the remote computer 95 is shown. As shown, the remote computer 95 includes a touch-sensitive user interface (not labeled) that allows hospital personnel such as a nurse to not only view the patient handling device data transmitted to the network 97 from the patient handling device 20, but also remotely activate features of the patient handling device 20 such as a scale, the bed exit system, brakes, articulation locks, and the like. The user interface may also include configuration controls to allow the users to set the desired state of the patient handling device 20.

The display 124 may also include amber 126 and green 128 indicators activated in the same manner as the alert and normal lamps 86, 92 on the patient handling device 20. Audible alarms may also be provided at the remote computer 95 or other locations to indicate whether the patient handling device 20 is in a desired or undesirable state or configuration.

The remote computer 95 may be in communication with a portable device (e.g., cellular phones, PDAs, pagers, etc.)

to deliver information about one or more patient handling devices 20 to a user. This information may include not only that an alarm has occurred, but the exact nature of the alarm. For instance, the portable device may display data similar to that displayed on the display 74 of the footboard control panel 68.

Obviously, many modifications and variations of the present invention are possible in light of the above teachings. The invention may be practiced otherwise than as specifically described within the scope of the appended claims.

What is claimed is:

1. A patient handling device comprising:
   a frame for supporting a mattress, the frame having a deck with at least one articulateable portion;
   a siderail mounted relative to the frame;
   an actuator for adjusting the at least one articulateable portion between a plurality of angular positions;
   a controller in communication with the actuator;
   a patient control in communication with the controller and configured to allow a patient to control the actuator to move the articulateable portion between the plurality of angular positions; and
   a caregiver control configured to allow a caregiver to control the actuator to move the articulateable portion between the plurality of angular positions, said caregiver control including a user operated position lock control, said caregiver control in communication with the controller, when actuated the lock control generating a position lock signal, when the lock control is actuated by a caregiver to generate the position lock signal the controller is configured to prevent the movement of the articulateable portion into restricted range of angular positions while permitting the patient control and the caregiver control to move the articulateable portion to a permitted subset of the plurality of angular positions thereby reducing the range of angular positions a patient and a caregiver can move the articulateable portion using the patient control or the caregiver control from the plurality of angular positions, wherein when the articulateable portion is in the restricted range of angular positions and the position lock control is actuated, the controller actuates the actuator to move the articulateable portion to the range of the permitted subset of the plurality of angular positions in response to the position lock signal.

2. The patient handling device according to claim 1, wherein the deck includes a head end portion forming the at least one articulateable portion, the controller limiting operation of the actuator to adjust the angular position of the head end portion to the permitted subset of angular positions.

3. The patient handling device according to claim 1, further comprising a display for displaying the angular position of the articulateable portion.

4. The patient handling device according to claim 1, wherein the permitted subset of angular positions is reconfigurable by a caregiver to change the range of the permitted angular positions for the patient control and the caregiver control.

5. The patient handling device according to claim 1, wherein the lock control is a pushbutton.

6. The patient handling device according to claim 2, wherein the permitted subset of angular positions comprises angles of greater than about 30 degrees.

7. The patient handling device according to claim 1, further comprising a position sensor, the controller in communication with the position sensor to detect when the articulateable portion is out of the range of the permitted subset of angular positions.

8. A method of operating the patient handling device of claim 1, the method comprising the steps of:
   receiving an actuator control signal to adjust the head end portion between a plurality of angular positions;
   sensing an angular position of the head end portion;
   receiving a position lock signal; and
   preventing operation of the actuator and thereby preventing adjustment of the head end portion to at least one restricted angular position in response to receiving the position lock signal.

9. A method as set forth in claim 8 further comprising the step of operating the actuator to position the head end portion to a permitted angular position in response to receiving the position lock signal.

10. The patient handling device according to claim 1, further comprising a lamp module to generate light with a first color and to generate light with a second color different than the first color; and
   the controller in communication with the lamp module, the controller configured to detect patient handling device conditions at the patient handling device, each of the patient handling device conditions having a desired state, when all of the monitored patient handling device conditions are in their desired state the controller is configured to control the lamp module to generate light with the first color to provide a unified indication that all of the monitored conditions are in their desired state, and when one of the monitored patient handling device conditions is not in its desired state the controller is configured to control the lamp module to generate light with the second color.

11. The patient handling device of claim 10, the lamp module comprising a housing with a first light source and a second light source located in the housing.

12. The patient handling device of claim 11, wherein the light emitted from the housing is a function of which light source is illuminated.

13. The patient handling device of claim 10, wherein the lamp module is located at a foot end of the patient handling device.

14. The patient handling device of claim 13, further comprising a footboard, the lamp module being mounted to the footboard.

15. The patient handling device of claim 11, wherein each of the light sources comprises a light emitting diode.

16. The patient handling device of claim 10, further comprising a mattress supported on the deck, wherein the lamp module is oriented to direct light outwardly from the patient handling device beneath an upper surface of the mattress wherein the light is not directed toward a patient supported on the patient handling device.

17. The patient handling device of claim 10, further comprising a plurality of sensors, the sensors detecting the patient handling device conditions.

18. The patient handling device of claim 17, wherein the sensors comprise at least two sensors selected from the group consisting of: a siderail switch, a brake sensor, a load cell, a bed exit sensor, a lockout sensor, an angle sensor, and a height sensor.

19. The patient handling device of claim 10, wherein the patient handling device conditions include at least two conditions selected from the group consisting of: a position of at least one siderail of the patient handling device; an angular position of the deck; a height of the deck; the activation of a brake of the patient handling device; and a state of a bed exit system of the patient handling device.

20. The patient handling device of claim 1, wherein the caregiver control comprises a control panel, and the position lock control comprises a button on a touch screen on the control panel.

* * * * *